(12) United States Patent
Chung

(10) Patent No.: US 6,338,347 B1
(45) Date of Patent: Jan. 15, 2002

(54) BLOOD CIRCULATION STIMULATOR

(76) Inventor: Yun-Yin Chung, 11/F-29, No. 164, Minchuan Rd., Taichung (TW)

( * ) Notice: Subject to any disclaimer, the term of this patent is extended or adjusted under 35 U.S.C. 154(b) by 0 days.

(21) Appl. No.: 09/542,915

(22) Filed: Apr. 4, 2000

(51) Int. Cl.⁷ .................................................. A61N 1/00
(52) U.S. Cl. ........................ 128/907; 600/9; 607/115; 607/145; 607/148
(58) Field of Search ................. 128/907; 601/15; 607/115, 139, 144–147, 149–151; 600/9

(56) References Cited

U.S. PATENT DOCUMENTS

| | | | | |
|---|---|---|---|---|
| 4,262,672 A | * | 4/1981 | Kief | 128/329 |
| 4,763,657 A | * | 8/1988 | Chen et al. | 128/422 |
| 4,915,110 A | * | 4/1990 | Kitov | 128/783 |
| 5,012,816 A | * | 5/1991 | Lederer | 128/735 |
| 5,030,196 A | * | 7/1991 | Inoue | 600/14 |
| 5,385,150 A | * | 1/1995 | Ishikawa | 128/735 |
| 5,607,461 A | * | 3/1997 | Lathrop | 607/75 |

* cited by examiner

Primary Examiner—Justine R. Yu
(74) Attorney, Agent, or Firm—Rosenberg, Klein & Lee

(57) ABSTRACT

A blood circulation stimulator is constructed to include a bottom cover shell, a top cover shell covered on the bottom cover shell and holding a battery set, a contact circuit board mounted inside the bottom cover shell to hold a plurality of spring-supported magnetic rod members and a plurality of electric current discharge rod members, and an electric current generator mounted in the top cover shell and controlled to output a low voltage electric current to the contact circuit board and then the electric current discharge rod members for stimulating the blood circulation of a person, the spring-supported magnetic rod members and the electric current discharge rod members each having a bottom end extending out of the bottom cover shell through a respective through hole on the bottom cover shell.

3 Claims, 4 Drawing Sheets

BLOOD CIRCULATION STIMULATOR

BACKGROUND OF THE INVENTION

The present invention relates to a blood circulation stimulator, and more particularly to such a blood circulation stimulator, which discharges magnetic waves and a low voltage electric current to stimulate the circulation of blood when touching the acupuncture points on the body of a person or moved over the body of the person FIG. 1 illustrates a blood circulation stimulator according to the prior art. This structure of blood circulation stimulator comprises a pen-base body 10, a discharge needle 11 extended out of the front end of the pen-base body 10, and an electric cable 12 extended out of the rear end of the pen-base body 10 and connected to an AC adapter (not shown). When in use, the discharge needle 11 is pressed on an acupuncture point on the body of a person, enabling a low voltage electric current to be discharged into the acupuncture point to stimulate the circulation of blood. This structure of blood circulation stimulator is not satisfactory in function. Because the blood circulation stimulator has only one discharge needle 11, it can only stimulate one acupuncture point at a time. When in use, the discharge needle 11 must be accurately pressed on the selected acupuncture point. However, it is not easy to an ordinary people to accurately press the discharge needle 11 on the acupuncture point. Furthermore, this structure of blood circulation stimulator does not provide magnetic waves to stimulate blood circulation.

SUMMARY OF THE INVENTION

The present invention has been accomplished under the circumstances in view. It is one object of the present invention to provide a blood circulation stimulator, which can easily be operated by an ordinary person without much learning. It is another object of the present invention to provide a blood circulation stimulator, which provides magnetic waves and a low voltage electric current to stimulate the circulation of blood of the person who receives the treatment. To achieve these and other objects of the present invention, there is provided a blood circulation stimulator comprising a bottom cover shell, a top cover shell covered on the bottom cover shell and holding a battery set, a contact circuit board mounted inside the bottom cover shell to hold a plurality of spring-supported magnetic rod members and a plurality of electric current discharge rod members, and an electric current generator mounted in the top cover shell and controlled to output a low voltage electric current to the contact circuit board and then the electric current discharge rod members for stimulating the blood circulation of a person. The spring-supported magnetic rod members and the electric current discharge rod members each have a bottom end extending out of the bottom cover shell through a respective through hole on the bottom cover shell.

DETAILED DESCRIPTION OF THE PREFERRED EMBODIMENT

Figure 1:
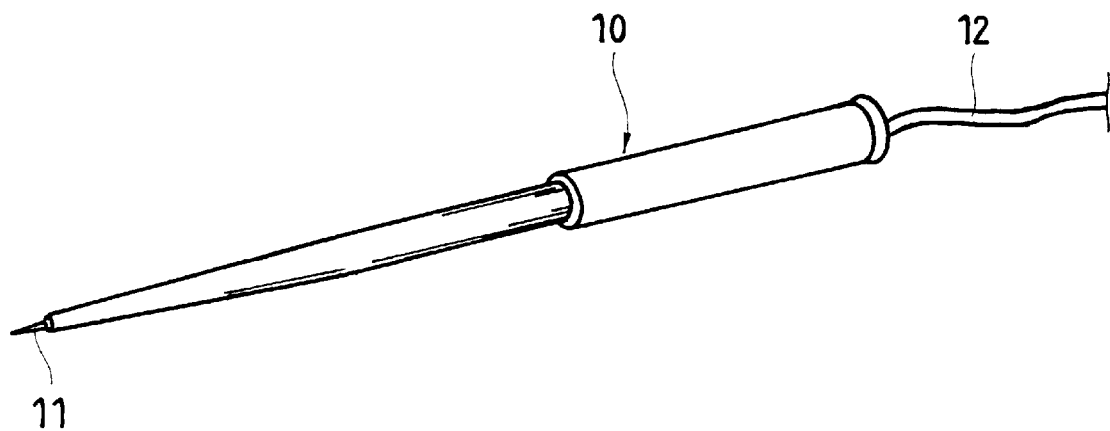
FIG. 1 is a blood circulation stimulator according to the prior art.
Figure 2:
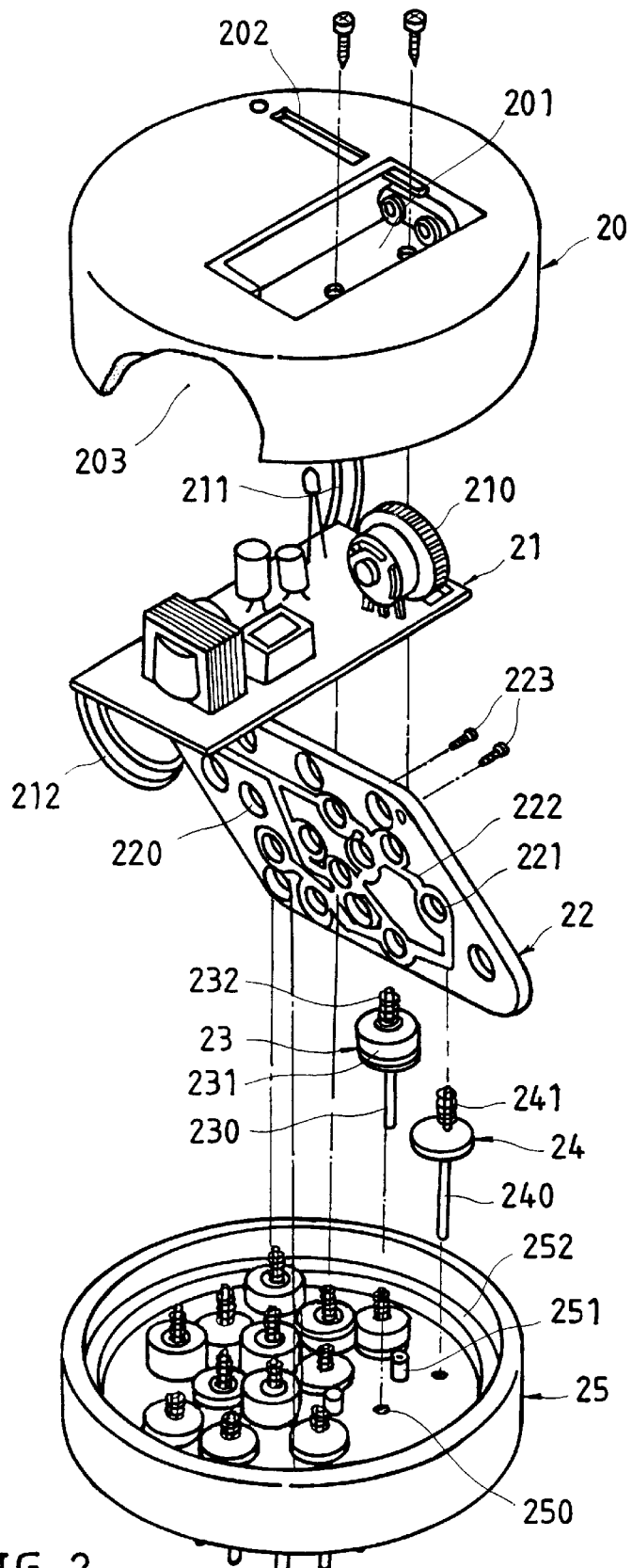
FIG. 2 is an exploded view of a blood circulation stimulator according to the present invention.
Figure 3:
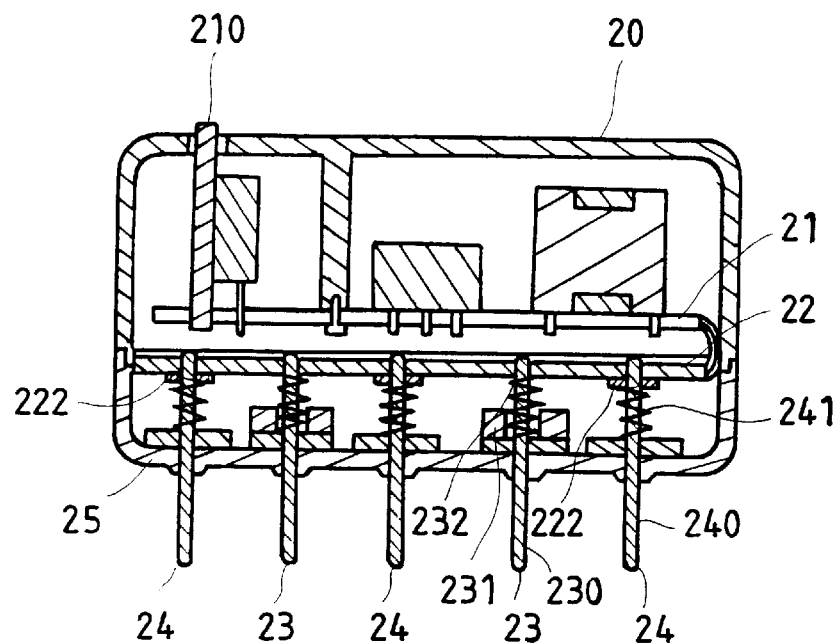
FIG. 3 is a sectional assembly view of the blood circulation stimulator shown in FIG. 2.

Referring to FIGS. 2 and 3, a blood circulation stimulator is shown comprised of a top cover shell 20, an electric current generator 21, a contact circuit board 22, a plurality of magnetic rod members 23, a plurality of electric discharge rod members 24, and a bottom cover shell 25.

The top cover shell 20 comprises a top battery chamber 201, which holds a battery set (not shown), an elongated slot 202, and a bottom-receiving chamber 203, which receives the electric current generator 21. The electric current generator 21 is comprised of an electric current generating circuit assembly, a rotary current adjustment knob 210, and conductors 211 and 212 respectively connected to the battery set in the top battery chamber 201 and the contact circuit board 22. The contact circuit board 22 comprises a plurality of through holes 220, which receives the magnetic rod members 23, a plurality of contact holes 221, which receive the electric discharge rod members 24, and a plurality of film conductors 222 connecting the contact holes 221. The magnetic rod members 23 each comprise a metal pin 230, a cylindrical magnet 231 fixedly mounted on the metal pin 230, and a spring 232 mounted on the metal pin 230 and supported above the cylindrical magnet 231. The electric discharge rod members 24 each comprise a collared metal pin 240, and a spring 241 mounted on the metal pin 240 and supported above the collar on the metal pin 240. The bottom cover shell 25 fits the top cover shell 20, comprising a plurality of through holes 250 corresponding to the through holes 220 and contact holes 221 on the contact circuit board 22, an annular inside mounting flange 252, and a plurality of fixed nuts 251.

The assembly process of the present invention is outlined hereinafter with reference to FIGS. 2 and 3 again, the magnetic rod members 23 and the electric discharge rod members 24 are respectively mounted in the bottom cover shell 25, enabling the metal rods 230 and 240 of the magnetic rod members 23 and electric discharge rod members 24 to be respectively extended out of the bottom cover shell 25 through the through holes 250, and then the circuit board 22 is supported on the annular inside mounting flange 252 inside the bottom cover shell 25 and fixedly fastened to the fixed nuts 251 by screws 223, enabling the metal rods 230 and 240 of the magnetic rod members 23 and electric discharge rod members 24 to be respectively engaged into the through holes 220 and contact holes 221 on the circuit board 22, and then the top cover shell 20 is covered on the bottom cover shell 25 to hold the electric current generator 21 on the inside, enabling the conductors 211 and 212 of the electric current generator 21 to be respectively connected to the battery set in the top battery chamber 201 and the contact circuit board 22. When assembled, the rotary current adjustment knob 210 extends out of the top cover shell 20 through the elongated slot 202, and the springs 232 and 241 impart a downward pressure to the respective rod members 23 and 24.

Figure 4:
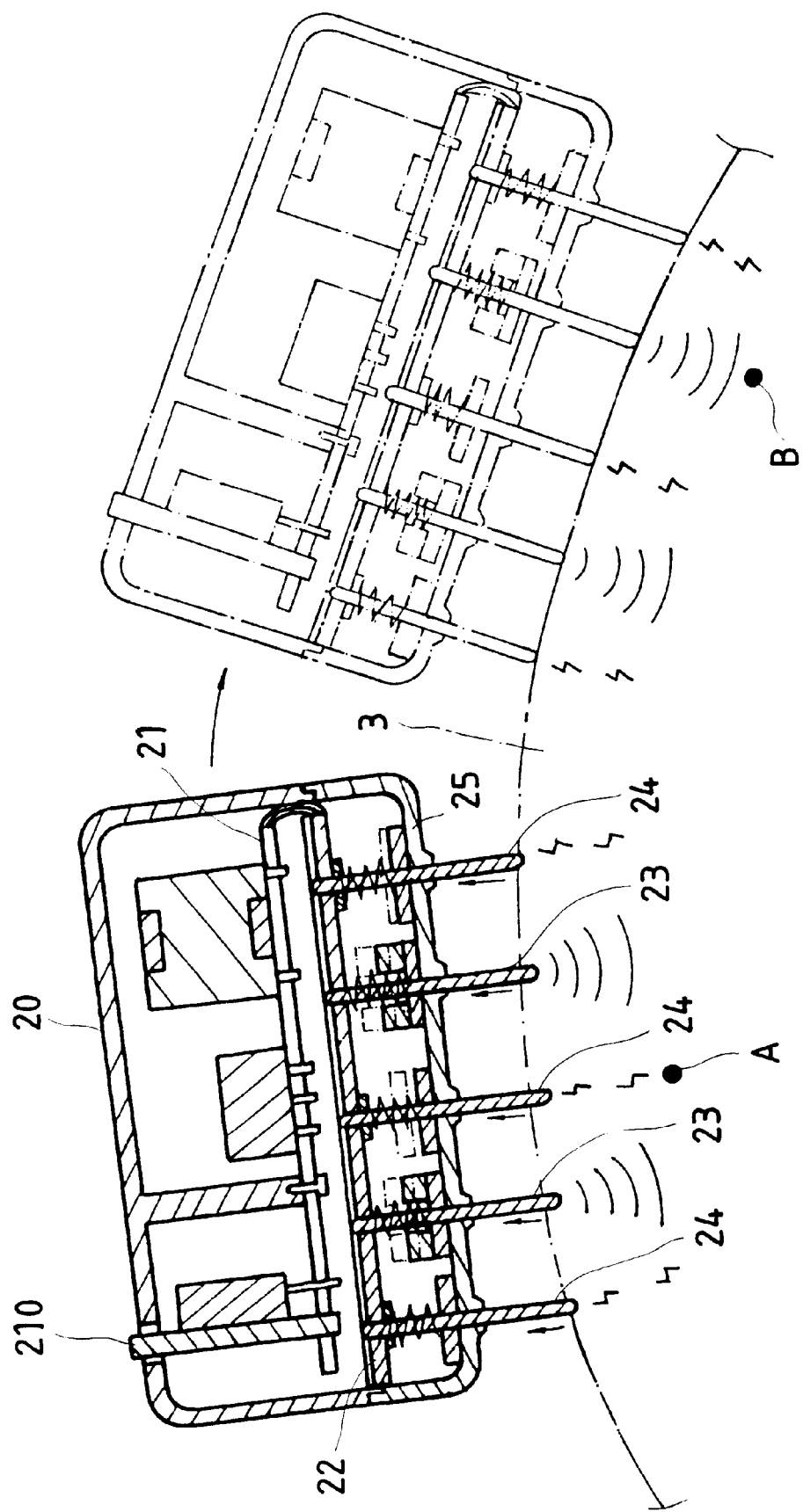
FIG. 4 shows an application example of the present invention.

Referring to FIG. 4, when in use, the rotary current adjustment knob 210 is operated to turn on the electric current generator 21, causing it to output a low voltage electric current to the contact holes 221 and the electric current discharge rod members 24. When contacting the acupuncture points A and B of the body 3 with the metal rods 230 and 240 of the magnetic rod members 23 and electric discharge rod members 24, the acupuncture points A and B of the body 3 are stimulated with magnetic waves and a low voltage electric current, and therefore the circulation of blood is stimulated. Because the rod members 23 and 24 are supported on the respective springs 232 and 241, the blood circulation stimulator can be smoothly moved over the skin without hurting the body 3. Further, the rotary current adjustment knob 210 can be controlled to provide selective current to the electric discharge rod members 24.

Figure 5:
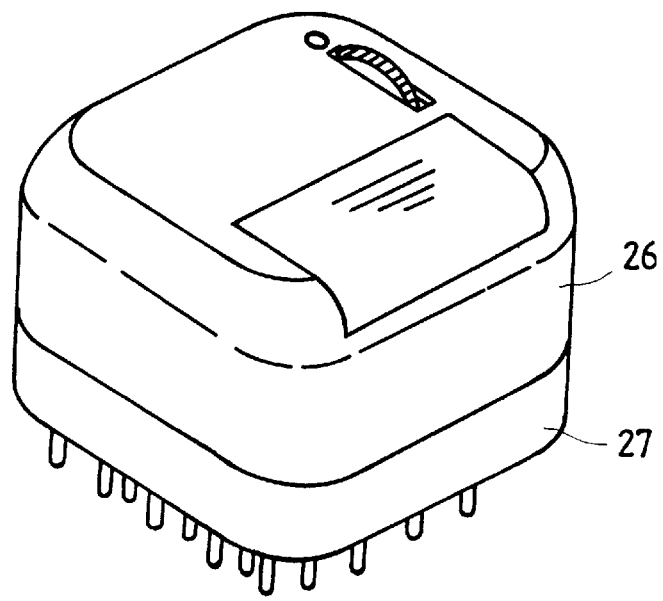
FIG. 5 is an elevational view of an alternate form of the blood circulation stimulator according to the present invention.

FIG. 5 shows an alternate form of the blood circulation stimulator. According to this embodiment, the top cover shell 26 and the bottom cover shell 27 have a square configuration.

It is to be understood that the drawings are designed for purposes of illustration only, and are not intended for use as a definition of the limits and scope of the invention disclosed.

What the invention claimed is:

1. A blood circulation stimulator comprising:

a bottom cover shell, said bottom cover shell comprising a plurality of through holes, a plurality of fixed nuts, and an annular inside mounting flange;

a top cover shell covered on said bottom cover shell, said top cover shell comprising a bottom receiving chamber, a top battery chamber, which receives a battery set, and an elongated slot;

a contact circuit board supported on said annular inside mounting flange inside said bottom cover shell and fixedly fastened to said fixed nuts with screws, said contact circuit board comprising a plurality of through holes, a plurality of contact holes, and a plurality of film conductors connecting said contact holes;

an electric current generator mounted in the bottom receiving chamber inside said top cover shell and connected between the battery set in said top battery chamber of said top cover shell and the contact holes of said contact circuit board with conductor means and controlled to output a low voltage electric current to said contact holes, said electric current generator comprising a rotary current control knob extended out of the elongated slot on said top cover shell for operation with the hand to control the output of said low voltage electric current to said contact holes;

a plurality of magnetic rod members respectively positioned in the through holes on said contact circuit board and the through holes on said bottom cover shell, said magnetic rod members each comprising a metal pin having a top end inserted into one through hole on said contact circuit board and a bottom end extending out of said bottom cover shell through one through hole on said bottom cover shell, a cylindrical magnet fixedly mounted on the respective metal pin, and a spring mounted on the metal pin of the respective magnetic rod member and supported between said cylindrical magnet and said contact circuit board; and a plurality of electric discharge rod members respectively positioned in the through holes on said contact circuit board and the contact holes on said bottom cover shell for transmitting said low voltage electric current from said contact holes to a person's body to stimulate the person's blood circulation, said electric discharged rod members each comprising a metal pin having a top end disposed in contact with one contact hole on said contact circuit board and a bottom extending out of said bottom cover shell through one through hole on said bottom cover shell, and a spring supported between said contact circuit board and a part of the metal pin of the corresponding electric current discharge member.

2. The blood circulation stimulator of claim 1 wherein said top cover shell and said bottom cover shell have a circular configuration.

3. The blood circulation stimulator of claim 1 wherein said top cover shell and said bottom cover shell have a square configuration.

* * * * *